United States Patent
Ruiz, III

(10) Patent No.: US 9,155,829 B2
(45) Date of Patent: Oct. 13, 2015

(54) DISPOSABLE SINGLE DOSAGE STERILE SALINE NASAL SPRAY SYSTEM

(71) Applicant: Leopoldo Ruiz, III, Laredo, TX (US)

(72) Inventor: Leopoldo Ruiz, III, Laredo, TX (US)

( * ) Notice: Subject to any disclaimer, the term of this patent is extended or adjusted under 35 U.S.C. 154(b) by 215 days.

(21) Appl. No.: 13/872,088

(22) Filed: Apr. 27, 2013

(65) Prior Publication Data

US 2014/0323973 A1    Oct. 30, 2014

(51) Int. Cl.
*A61M 15/08* (2006.01)
*A61M 3/02* (2006.01)
*A61H 35/04* (2006.01)
*A61K 9/00* (2006.01)
*A61M 11/00* (2006.01)

(52) U.S. Cl.
CPC ............. *A61M 3/0262* (2013.01); *A61H 35/04* (2013.01); *A61K 9/0043* (2013.01); *A61H 2201/1253* (2013.01); *A61H 2201/1688* (2013.01); *A61M 11/008* (2014.02); *A61M 15/08* (2013.01)

(58) Field of Classification Search
CPC ... A61M 3/0262; A61M 15/08; A61M 11/00; A61M 15/0028; A61M 15/0031; A61M 11/008; B05B 11/00; A61K 9/0043
See application file for complete search history.

(56) References Cited

U.S. PATENT DOCUMENTS

| | | | |
|---|---|---|---|
| 6,241,124 B1 * | 6/2001 | Hoyt | 222/143 |
| 6,294,178 B1 * | 9/2001 | Weinstein et al. | 424/400 |
| 6,528,081 B1 * | 3/2003 | Zellner | 424/434 |
| 6,669,059 B2 * | 12/2003 | Mehta | 222/211 |
| 7,810,495 B2 * | 10/2010 | Gumaste | 128/203.23 |
| 7,862,548 B2 * | 1/2011 | Javer et al. | 604/310 |
| 8,048,023 B2 * | 11/2011 | Hoke et al. | 604/94.01 |
| 8,092,434 B2 * | 1/2012 | Harlan et al. | 604/275 |
| 8,337,906 B2 * | 12/2012 | Zinreich et al. | 424/680 |
| 8,343,114 B2 * | 1/2013 | Mehta | 604/275 |

* cited by examiner

*Primary Examiner* — Aarti B Berdichevsky

(57) ABSTRACT

Pure sodium chloride is dissolved in sterile distilled water to form a sterile pure saline solution. A hermetically sealed disposable spray container holds a single measured dosage of the solution for fully rinsing and cleansing a nasal passageway. The measured dosage is sufficient for rinsing and cleansing the nasal passage and harmless if the measured dosage mistakenly enters the lungs or sinuses or stomach of the user.

3 Claims, 2 Drawing Sheets

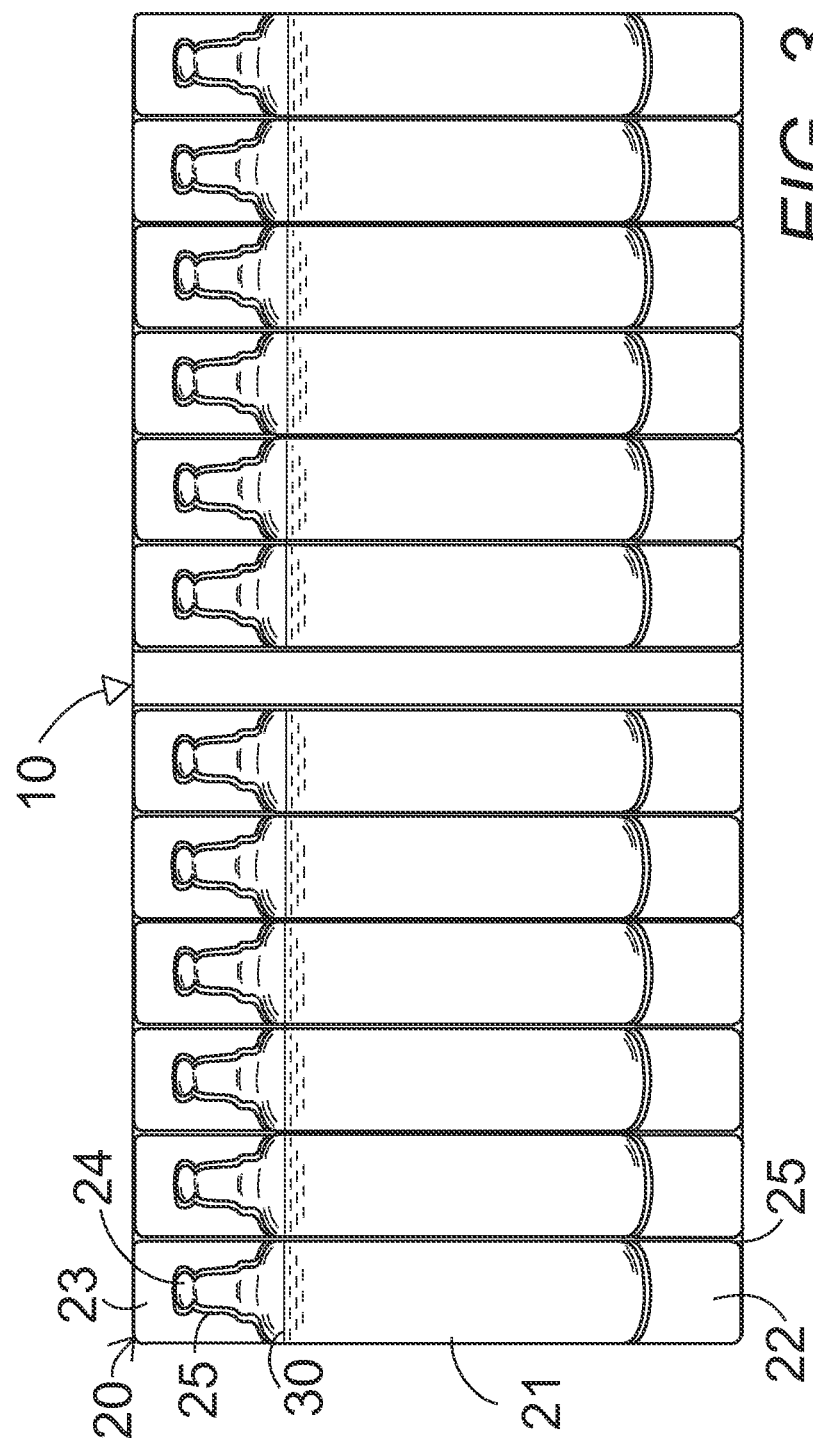

DISPOSABLE SINGLE DOSAGE STERILE SALINE NASAL SPRAY SYSTEM

CROSS-REFERENCE TO RELATED APPLICATIONS

Not Applicable.

STATEMENT REGARDING FEDERALLY SPONSORED RESEARCH OR DEVELOPMENT

Not Applicable.

THE NAMES OF THE PARTIES TO A JOINT RESEARCH OR DEVELOPMENT

Not Applicable.

BACKGROUND OF THE INVENTION

1. Field of the Invention

The present invention relates to systems for spraying nasal passages and in particular to a sterile nasal passageway cleansing solution comprising pure sodium chloride dissolved in sterile distilled water to form a sterile pure saline solution having a salinity (preferably 0.9% to match body fluid salinity) which is harmless to a human body and a sterility which will not cause infection; the sterile saline solution housed in a hermetically sealed disposable spray container holding a single measured dosage of the sterile saline solution for fully rinsing and cleansing a nasal passageway of a user when sprayed into the nasal passageway from the container, the measured dosage sufficient for rinsing and cleansing the nasal passage and harmless if the measured dosage mistakenly enters the lungs or sinuses or stomach of the user.

2. Description of Related Art Including Information Disclosed Under 37 CFR 1.97 and 1.98

When exposed to dust, pollen, viruses, bacteria, industrial pollutants, smoke, toxins, or any other particulates or harmful substances in the air, the nasal passages can become blocked or irritated or infected. It is desirable to clean the nasal passages as soon as possible after such exposure to prevent breathing problems, allergic reactions, tissue damage, infections and other complications from such exposure. It is also desirable to clean the nasal passages of natural fluids and other matter which the body eliminates through the nose.

Prior art patents for nasal spraying primarily contain spray solutions containing many ingredients, such as antihistamine sprays, usually for medicinal purposes, and are housed in multiple use containers. Prior art for strictly cleaning nasal passages often provide extra means for draining the nasal passageway and do not provide pure sterile saline solutions. Reusable containers can allow contamination of the container and spray solution which may produce infections. Most prior art spray solutions also contain buffers and preservatives to prolong shelf life and many other potentially harmful ingredients which are not necessary for the desired purpose of cleansing the nostrils of unwanted matter.

In prior art containers which hold and can spray more than the amount needed for cleansing a nasal passage, there is a danger of accidentally spraying too much thereby inundating lungs, sinuses or other internal passages with too much fluid which may cause serious health problems.

U.S. Pat. No. 1,023,499, issued Apr. 16, 1912 to Bell, provides a compressible capsule which is adapted to discharge its contents in the form of a blast, spray, or stream, a self-contained ejector in which fluid, semi-fluid or comminuted matter is hermetically sealed until desired for immediate use; and the invention consists essentially in a collapsible capsule in which are incorporated filaments which may be extracted to form holes for the discharge of the contents of the capsule. While applicable to an infinite variety of uses and purposes my capsule is designed more especially as a one dose or application device to be discarded after use.

U.S. Pat. No. 7,810,495, issued Oct. 12, 2010 to Gumaste, discloses a blister pack for use with inhalation therapy inhalers comprises an elongate bottom element having an overlying top element defining a plurality of spaced top crowned areas containing powder or liquid medications or drugs.

U.S. Pat. No. 6,294,178, issued Sep. 25, 2001 to Weinstein et al, is for a sinusitis treatment system having an oral dosage constituent, a topical nasal dosage constituent, indicia and instructions for administration of the oral dosage constituent and the topical nasal dosage constituent as an at least ten-day sinusitis treatment regimen.

U.S. Pat. No. 8,092,434, issued Jan. 10, 2012 to Harlan et al, provides a nasal passage washing device including a pliable body including an open top; and an applicator cap removably attached to the pliable body to cover and uncover the open top. The applicator cap includes an applicator tip having a substantially frustoconical configuration sized and shaped for receipt at least partially within a nostril of a user for sealing engagement therewith, the applicator tip including a hole to transfer washing solution there through, a washing solution transfer tube in communication with the hole of the applicator tip and a bottom of an inside of the pliable body to transfer washing solution from the bottom of the inside of the pliable body to the hole of the applicator tip, and a one-way air valve that only allows air flow into the pliable body through the one-way air valve and does not allow air flow and washing solution flow out of the pliable body through the one-way air valve.

U.S. Pat. No. 8,048,023, issued Nov. 1, 2011 to Hoke et al, provides systems and methods for nasal irrigation are provided in which a nasal irrigation device includes a source of saline solution, an effluent receptacle, a nasal interface, a vacuum source, a fluid passageway to communicate the source of saline solution with the effluent receptacle through the nasal interface and a nasal cavity of the user, and a switch and valve assembly for selectively controlling the vacuum source and flow of the saline solution through the fluid passageway. The saline solution source is disposed relative to the device to provide gravitational inducement of saline solution to the nasal interface in engagement to the device user's nostrils. A combination of the gravitational inducement and the relative vacuum from the effluent receptacle generates a fluid flow for irrigating, cleansing and massaging the nasal cavity and ostia of a user. The entire device is assembled as a hand-held device for convenient lifting and disposal against the user's nostrils.

U.S. Pat. No. 6,528,081, issued Mar. 4, 2003 to Zellner, claims the spray liquid of a nasal spray formed by a hyperosmotically adjusted water saline solution with a common salt content of 1 to 4% by weight. It furthermore contains various essential oils.

U.S. Pat. No. 8,337,906, issued Dec. 25, 2012 to Zinreich et al, describes a nasal spray solution for use as a nasal spray and methods of using the solution are disclosed. The nasal spray solution moisturizes nasal passages and alleviates nasal dryness. The solution includes a hypotonic saline solution, wherein the saline solution is hypotonic with respect to cells of the nasal mucosa of the nasal passages, a buffering agent, a lubricating agent, and an anti-microbial agent.

U.S. Pat. No. 6,669,059, issued Dec. 30, 2003 to Mehta, indicates an apparatus and method for preparing a pH balanced saline solution and using the saline solution for rinsing a nasal passage. The apparatus includes a container having flexible sidewalls and an opening for a removable cap. The cap has a rounded convex upper portion curving away from an opening at the cap's uppermost surface and has a conduit in the cap's interior, which conduit extends into the container when the apparatus is fully assembled or is connected to a tube that extends in the container. A saline solution is prepared by adding sodium chloride and sodium bicarbonate to distilled water. The sidewalls of the container, filled with the saline solution, are compressed to urge the saline solution through the conduit, or tube and conduit, and through the opening in the cap and into a nasal passage, the cap being pressed against a nostril to provide a comfortable and effective seal.

U.S. Pat. No. 7,862,548, issued Jan. 4, 2011 to Javer et al, puts forth nasal irrigation device includes a container for storing nasal cleansing fluid, a spout having a connecting end, a nose engaging end and a spout passage, the connecting end of the spout being removably coupled to the container to allow the spout passage to receive nasal cleansing fluid from an opening of the container, the spout having a curved portion for directing nasal cleansing fluid toward a nasal passageway of a user when the container is clear of a nasal discharge path, the spout passage being continually open and unobstructed. The container is partially collapsible to force nasal cleansing fluid through the spout passage and into the nasal passageway.

U.S. Pat. No. 8,343,114, issued Jan. 1, 2013 to Mehta, concerns a device for nasal lavage which ejects a gently flow of fluid under pressure. The low pressure fluid stream is more comfortable for a user than a high pressure fluid stream delivered by some types of pressurized cans of solution.

U.S. Patent Application No. 2011/0057055, filed Oct. 9, 2009 by Wong, claims a single dose nasal spray pump includes a reservoir configured for holding a single dose of material to be dispensed, the reservoir extending between a closed end and an open end; a cap to be configured to be disposed over the open end of the reservoir, the cap including an aperture; a stem extending between an outlet end and a lower end, the stem having a conduit extending from the outlet end of the stem to a conduit inlet at or adjacent the lower end of the stem; and a piston disposed about the stem and configured for movement between a first position wherein the piston seals or substantially seals the conduit inlet and a second position wherein the piston is remote from the conduit inlet; wherein the stem is configured for movement from a first stem position wherein the piston is disposed in the reservoir in the first piston position and a second stem position wherein the stem is moved toward the closed end of the reservoir such that the piston is moved.

What is needed is a sterile nasal passageway cleansing solution comprising pure sodium chloride dissolved in sterile distilled water to form a pure sterile saline solution having a salinity matching natural body fluid salinity for safely cleansing nasal passages without added ingredients so the solution is harmless to a human body and will not cause infection and providing the solution in a single dosage container with an optimum amount of the spray solution to cleanse the nostrils without too much fluid entering the nasal passages, sinuses, and lungs.

BRIEF SUMMARY OF THE INVENTION

An object of the present invention is to provide a disposable single dosage nasal sterile saline solution spray system for rinsing and cleansing a nostril of a user containing a sterile nasal passageway cleansing solution comprising pure sodium chloride dissolved in sterile distilled water to form a sterile pure saline solution having a salinity (preferably 0.9% to match body fluid salinity) which is harmless to a human body and a sterility which will not cause infection.

An additional object of the present invention is to house the sterile saline solution in a hermetically sealed disposable spray container holding a single measured dosage of the sterile saline solution for fully rinsing and cleansing a nasal passageway of a user when sprayed into the nasal passageway from the container, the measured dosage sufficient for rinsing and cleansing the nasal passage and harmless if the measured dosage mistakenly enters the lungs or sinuses or stomach of the user.

A further object of the present invention comprises having the sterile saline solution sealed within the hermetically sealed container to provide the system with a long shelf life with no preservatives or buffers or other ingredients contained in the sterile saline solution.

One more object of the present invention is to provide a disposable container so that the container is disposed of after administering the single dosage, so that only the original sealed sterile saline solution is used in the nasal passageway and there is no solution left in storage in an unsealed container after using, thereby preventing the contamination of the solution that can occur in prior art nasal spraying systems.

In brief, pure sodium chloride is dissolved in sterile distilled water to form a sterile pure preferably 0.9% saline solution to match the salinity of body fluids. A hermetically sealed disposable spray container holds a single measured dosage of the solution for fully rinsing and cleansing a nasal passageway. The measured dosage is sufficient for rinsing and cleansing the nasal passage and harmless if the measured dosage mistakenly enters the lungs or sinuses or stomach of the user.

An advantage of the present invention is that it provides a saline solution spray system for rinsing and cleansing a nostril of a user, which has a salinity matching human body fluids.

Another advantage of the present invention is that it provides a single measured dosage sufficient for rinsing and cleansing the nasal passage and harmless if the measured dosage mistakenly enters the lungs or sinuses or stomach of the user.

An added advantage of the present invention is that it provides a sterile saline solution sealed within a hermetically sealed container to provide the system with a long shelf life with no preservatives or buffers or other ingredients contained in the sterile saline solution.

One more advantage of the present invention is that it provides a a container which is disposed of after administering the single dosage, so that only the original sealed sterile saline solution is used in the nasal passageway and there is no solution left in storage in an unsealed container after using.

BRIEF DESCRIPTION OF THE SEVERAL VIEWS OF THE DRAWINGS

These and other details of the present invention will be described in connection with the accompanying drawings, which are furnished only by way of illustration and not in limitation of the invention, and in which drawings:

FIG. 3 is an elevational view of a series of aligned disposable hermitically sealed single dosage containers for the sterile saline solution nasal spray of the present invention showing a dozen of the containers packaged together with a breakaway area in the molded plastic material between each pair of adjacent containers.

DETAILED DESCRIPTION OF THE INVENTION

Figure 1:
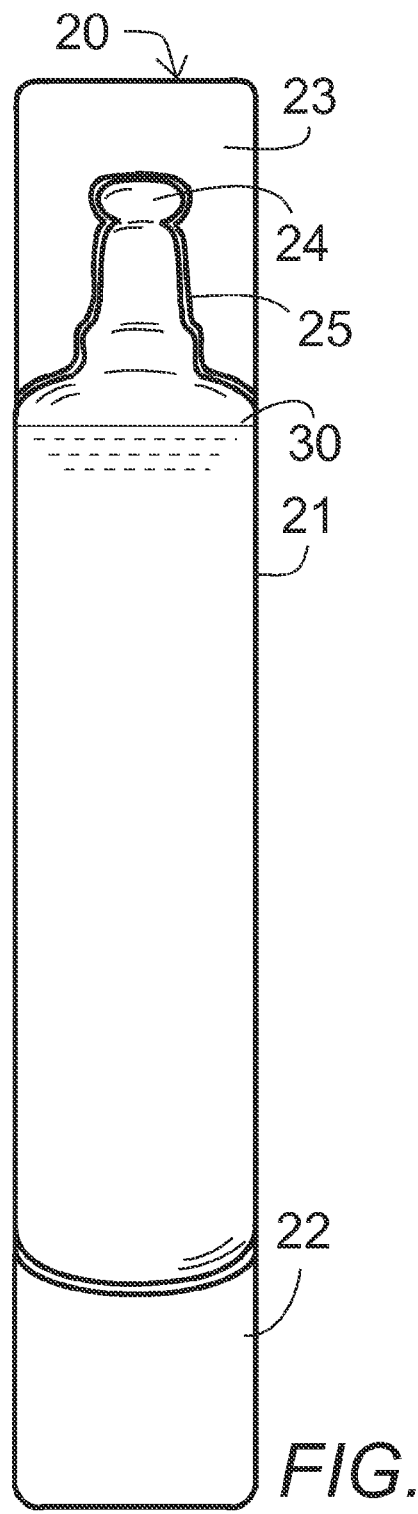
FIG. 1 is an elevational view of a disposable hermetically sealed single dosage container for the sterile saline solution nasal spray of the present invention.
Figure 2:
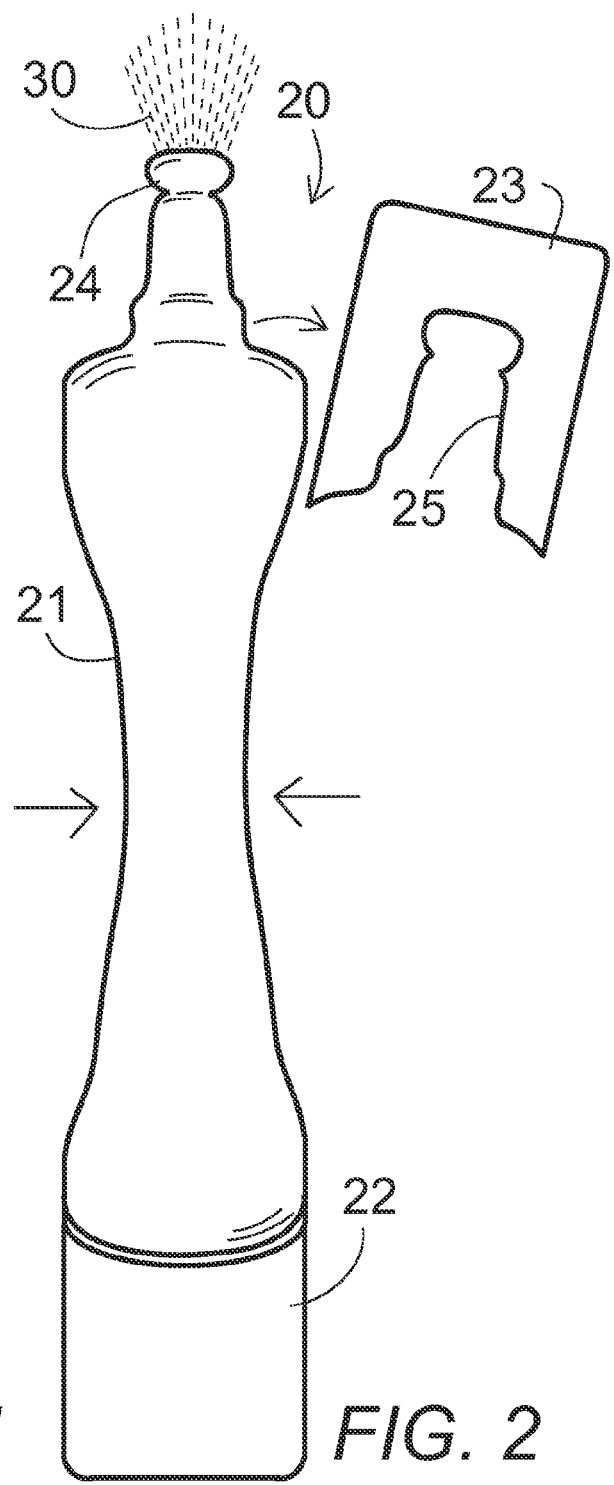
FIG. 2 is an elevational view of the disposable hermitically sealed single dosage container for the sterile saline solution nasal spray of the present invention of FIG. 1 showing the cover for the top opening broken away from the container exposing a spray nozzle and showing the body of the container being squeezed in and the solution being sprayed out of the top of the spray nozzle.

In FIGS. 1-3, a disposable single dosage nasal sterile saline solution 30 and spray system 10 comprising multiple single dose spray containers 20 interconnected by breakaway areas 25, shown in FIG. 3, for rinsing and cleansing a nostril of a user.

The system comprises a sterile nasal passageway cleansing solution 30 comprising pure sodium chloride dissolved in sterile distilled water to form a sterile pure saline solution having a salinity which is harmless to a human body and a sterility which will not cause infection. The sterile saline solution 30 is housed in a hermetically sealed disposable spray container 20 holding a single measured dosage of the sterile saline solution 30 for fully rinsing and cleansing a nasal passageway of a user when sprayed into the nasal passageway from the container 20 by squeezing the container as indicated by the arrows facing the container on opposing sides of the body 21 of the container to produce the saline solution spray 30 out of the top of the open nozzle 24, as shown in FIG. 2, with the breakaway tab nozzle cover 23 removed.

The measured dosage is sufficient for rinsing and cleansing the nasal passage and harmless if the measured dosage mistakenly enters the lungs or sinuses or stomach of the user. The sterile saline solution 30 sealed within the hermetically sealed container 20 provides the system with a long shelf life with no preservatives or buffers or other ingredients contained in the sterile saline solution.

The container 20 is disposed of after administering the single dosage, so that only the original sealed sterile saline solution 30 is used in the nasal passageway and there is no solution left in storage in an unsealed container after using.

The sterile saline solution 30 preferably comprises a quantity of pure sodium chloride dissolved in sterile distilled water to form a 0.9% sterile saline solution so that the sterile saline solution 30 has a salinity matching the natural normal salinity of human body fluids.

In FIG. 3, the system 10 comprises a plurality single dosages of the sterile saline solution 30 each housed in one of a series of hermetically sealed molded containers 20 formed as an interconnected series of breakaway single dosage containers, each container having a breakaway cap tab 23 for exposing an opening in the container for dispensing the single dosage of sterile saline solution 30 sprayed out of the nozzle 24 directly into a nasal passageway of a user.

The spray nozzle 24 tapers outwardly toward the end opening for spraying the inner walls of the nostrils of the user. The liquid dispersing spray opening nozzle 24 is preferably molded into an end of the container 20 for spraying the sterile saline solution 30 into a nostril of a user when the cap tab 23 is broken away, as shown in FIG. 2.

In use, a single dosage container 20 is broken away from the array of container forming the system package 10 and held by a bottom holding tab 22 while the top cap tab 23 is broken away. Then the top nozzle 23 is inserted into a bottom portion of the nostril of the user and the container squeezed, as in FIG. 2, to spray and clean the inner walls of the nasal passage.

It is understood that the preceding description is given merely by way of illustration and not in limitation of the invention and that various modifications may be made thereto without departing from the spirit of the invention as claimed.

What is claimed is:

1. A disposable single dosage nasal sterile saline solution spray system for rinsing and cleansing a nostril of a user, the system comprising:

a sterile nasal passageway cleansing solution comprising pure sodium chloride dissolved in sterile distilled water to form a sterile pure saline solution having a salinity matching body fluid salinity of a human body and having a sterility which will not cause infection; the sterile saline solution housed in a hermetically sealed disposable spray container holding a single measured dosage of the sterile saline solution adapted for rinsing and cleansing a nasal passageway of a user when sprayed into the nasal passageway from the container, the single measured dosage adapted for rinsing and cleansing the nasal passageway and adapted to cause no bodily harm if the single measured dosage mistakenly enters the lungs or sinuses or stomach of the user; the sterile saline solution sealed within the hermetically sealed container providing the system with a shelf life with no preservatives or buffers or other ingredients contained in the sterile saline solution; a spraying end of the hermetically sealed container having an end opening communicating with the single measured dosage of the sterile saline solution housed in the hermetically sealed disposable spray container, the end opening comprising a liquid dispersing spray nozzle opening tapering outwardly toward the end opening, the spray nozzle opening adapted to be inserted in a nostril of a user and adapted for spraying a dispersed spray of the sterile nasal passageway cleansing solution onto inner walls of the nostril of the user, the liquid dispersing spray nozzle opening molded into an end of the container, the hermetically sealed container further comprising a cap tab molded to the liquid dispersing spray nozzle opening with a break-away connection so that the cap tab is adapted to be broken away from the liquid dispersing spray nozzle opening and the hermetically sealed disposable spray container comprises a smooth liquid container portion adapted to be squeezed to spray the entire single measured dosage of the sterile nasal passageway cleansing solution out in a dispersed spray onto the inner walls of a nostril of the user leaving an empty container; the empty container adapted for being disposed of after administering the single dosage, so that the original sealed single dosage of the sterile nasal passageway cleansing saline solution is sprayed out to cleanse the nasal passageway of the user and there is no solution left in storage in an unsealed container after using; thereby providing a disposable single dosage nasal sterile saline solution spray system for rinsing and cleansing a nostril of a user.

2. The system of claim 1 wherein the sterile saline solution comprises a quantity of pure sodium chloride dissolved in sterile distilled water to form a 0.9% sterile saline solution so that the sterile saline solution has a salinity matching the natural normal salinity of human body fluids.

3. The system of claim 1 comprising a plurality of single dosages of the sterile nasal passageway cleansing saline solution each housed in one of a series of hermetically sealed molded containers formed as an interconnected series of breakaway single dosage containers, each container having a breakaway cap tab adapted for breaking away to expose the liquid dispersing spray nozzle opening in the container adapted for spraying the single dosage of sterile nasal passageway cleansing saline solution contained therein.

* * * * *